United States Patent [19]

Gresshoff et al.

[11] Patent Number: 5,124,504
[45] Date of Patent: Jun. 23, 1992

[54] NITRATE-TOLERANT SOYBEAN

[75] Inventors: Peter M. Gresshoff, Dickson; Bernard J. Carroll, Karringal; David L. McNeil, Kununurra, all of Australia

[73] Assignee: Lubrizol Genetics, Inc., Wickliffe, Ohio

[21] Appl. No.: 16,274

[22] Filed: Feb. 19, 1987

Related U.S. Application Data

[63] Continuation-in-part of Ser. No. 618,639, Jun. 6, 1984, abandoned.

[51] Int. Cl.$^5$ .................. A01H 1/04; C12N 15/00
[52] U.S. Cl. .................. 800/230; 800/DIG. 26; 435/172.1
[58] Field of Search ............... 435/172.1; 800/1, 230, 800/DIG. 26; 71/7

[56] References Cited

PUBLICATIONS

Harper et al. 1984, p. 537 In: Adv. Nitr. Fix. Res. (Veeger et al., eds.), Nijhoff: Wageningen, The Hague.
Jacobsen et al. 1984, Plant Sci. Lett. 33:337–344.
Kiang et al. 1975, Mutation Research 33:373–382.
Carroll et al. 1984, p. 589 in Advances in Nitrogen Fixation Research, Veeger et al., eds. Nijhoff: Wageningen, The Hague.
Betts et al. 1987, Crop Sci. 27:1156–1161.
Herridge et al. 1988, Plant Sci. 110:129–135.
Eskew et al. 1989, Crop Sci. 29:1490–1496.
Delves et al. 1987, Aust. J. Plant Physiol. 14:689–694.
Oswald et al. 1977, Physiol. Plant. 39:129–134.
Carroll, B. J. and P. M. Gresshoff (1983) Z. Pflanzenphysiol. 100:77–88.
Streeter, J. G. (1981) Plant Physiol. 68:840–844.
Nutman, P. S. (1981) in Current Perspectives in Nitrogen Fixation, Gibson and Newton (eds.) Australian Academy of Science, Canberra, Australia, pp. 194–204.

Heichel, G. H. et al. (1984) in Advances in Nitrogen Fixation Research, Veeger and Newton (eds.) Martinus Nijhoff/Dr. W. Junk (publishers), The Hague and Pudoc, Wageningen, p. 595.
Gelin, O. and S. Blixit (1964) Agri. Hort. Genet. 22:149–163.
Jacobsen, E. (1984) in Advances in Nitrogen Fixation Research, Veeger and Newton (eds.) Martinus Nijhoff/Dr. W. Junk (publishers), The Hague and Pudoc, Wageningen, p. 597.
Carroll et al. (1985) Proc. Natl. Acad. Sci. U.S.A. 82:4162–4166.
Carroll et al. (1985) Plant Physiol. 78:34–40.
Nutman, P. S. (1952) Annals of Botany 16:80–101.
Nutman, P. S. (1949) Anals of Botany 13:261–283.
Nutman, P. W. (1962) Proc. Royal Soc. Ser. 13 156:122–137.
Tudge, C. (1984) New Scientist 9:13–15.

(List continued on next page.)

*Primary Examiner*—David T. Fox
*Attorney, Agent, or Firm*—Greenlee and Winner

[57] ABSTRACT

Genetically manipulated soybeam varieties which display nitrate-tolerant nodulation and supernodulation are described. The soybean nodulation mutants of the present invention can be specifically prepared by induced mutagenesis followed by appropriate phenotype screening. Fifteen individual mutants having nitrate tolerant nodulation and/or supernodulation phenotypes have been isolated. Soybean varieties having the nodulation phenotypes of the present invention are useful in the development of novel and agronomically important varieties of soybean.

29 Claims, 4 Drawing Sheets

PUBLICATIONS

Kiang, L. C. and G. M. Halloran (1975) Mutation Res. 33:373–382.

Dreher, T. W. et al. (1980) Mutation Res. 71:201–206.

Lee, C. K. and G. M. Halloran (1982) Environ. & Experimental Bot. 22:75–79.

Wilcox, J. R. et al. (1984) J. Amer. Oil Chem. Soc. 61:97–100.

Gibson, A. H. and Harper, J. E. (1985) Crop Science 25:497–501.

Gremaud, M. F. and Harper, J. E. (1989) Plant Physiol. 89:169–173.

Carroll, B. J. and Gresshoff, P. M. (1986) Plant Physiol. 81:572–576.

E. Jacobsen (1984) Plant and Soil 82:427–438.

E. Jacobsen and H. Nydam (1983) Pisum Newsl. 15:31–32.

Jacobsen et al. (1985) in Nitrogen Fixation Research Progress, Evans et al. (eds.), Martinus Nijhoff Publishers, p. 43.

Meijer (1982), "Development of Leguminous Root Nodules" in Nitrogen Fixation vol. 2: Rhizobium (Boughton, ed.) Clarendon Press, Oxford, U.K., Chapter 10, pp. 311–331.

NITRATE-TOLERANT SOYBEAN

This is a continuation-in-part of U.S. patent application Ser. No. 618,639, filed Jun. 6, 1984, now abandoned.

FIELD OF THE INVENTION

The invention relates in general to leguminous plants, in particular soybean varieties, having the phenotypes of nitrate-tolerant nodulation, and of supernodulation. Novel, genetically modified nitrate-tolerant and supernodulating soybean plants are disclosed, distinguished from wild-type and domesticated cultivars in having the phenotype of nitrate-tolerant nodulation or of supernodulation. A method of plant breeding, for introducing the nitrate-tolerant nodulation and supernodulation traits into domestic cultivars is disclosed. Further, a process for genetic manipulation to produce and select for nitrate-tolerant plants or for supernodulating plants is disclosed. Plants having nitrate-tolerant nodulation are agronomically useful in that they are able to form effective root nodules at an earlier growth stage than conventional cultivars, in soils having endogenous nitrate. Early nodulation enhances the effectiveness of any added soil inoculant, and it prevents a growth lag commonly associated with the depletion of endogenous nitrate during plant growth and prior to the establishment of effective root nodules. Supernodulation similarly enhances the effectiveness of soil inoculants and contributes to decreased dependence on exogenous nitrogen sources.

BACKGROUND

The development of the symbiosis that results in nodule formation and nitrogen fixation is a complex process that involves genetic factors in both the bacterial symbiont and the host plant. Much work has been done to elucidate the genetic factors in Rhizobium that affect symbiosis. In contrast, only a few heritable host plant factors have been reported to influence the extent of symbiosis in legumes (Nutman (1981) in *Current Perspectives in Nitrogen Fixation Research*, Gibson and Newton (eds) Austr. Acad. Sci., Canberra, Australia, pp. 194–204). The most striking host variations in nodulation that have been observed are decreased nodulation or absence of nodulation. However, natural variants within existing germ plasms with enhanced nodulation have been demonstrated in some species of legumes (Gelin and Blixt (1964) Agri Hort. Genet. 22:149–163; Nutman (1953) Heredity 8:35–46; Duhigg et al. (1978) Crop Sci. 18:813–816; Heichel et al. (1984) in *Advances in Nitrogen Fixation Research*, Veeger and Newton (eds) Martinus Nijhof/Junk, The Hague Netherlands, p. 595; Imsande (1984) ibid. p. 596; Nutman et al. (1971) in *Biological Nitrogen Fixation in Natural and Agricultural Habitats*, Lie and Mulder (eds) (Plant and Soil special volume) Martinus Nijhoff, The Hague, Netherlands pp. 27–31; Mylton and Jones (1971) ibid. pp. 17–25).

Symbiotic nitrogen fixation in legumes can also be affected by environmental factors. One such factor that is particularly important is the level of nitrate in the soil. The development of symbiosis is inhibited by high soil nitrate concentrations. Suppression of symbiosis is manifested both in reduced nodule mass and in reduced nitrogenase activity per unit nodule mass (Carroll, B. J. and Gresshoff, P. M. (1983) Z. Pflanzenphysiol. 100:77–88; Streeter, J. G. (1981) Plant Physiol. 68:840–844). The mechanism of nitrate inhibition is not fully understood, but it is hypothesized either that nitrate reduction which limits carbohydrate availability results in limitation of nodule development or that the products of nitrate reduction, particularly nitrite, inhibit nitrogenase (Oghoghorie and Plate (1971) in *Biological Nitrogen Fixation in Natural and Agricultural Habitats*, Plant and Soil Special Volume, Lie and Mulder (eds) Nijhoff/Junk, The Hague, The Netherlands, p. 185–202; Trinchant and Rigaud (1980) Arch. Microbiol. 124:49–54; Rigaud and Puppo (1977) Biochim. Biophys. Acta 497:702–706). Minor differences in nodulation tolerance to nitrate have been demonstrated between host species (Carroll et al. (1984) in *Advances in Nitrogen Fixation Research*, Veeger and Newton (eds) Nijhoff/Junk, The Hague, The Netherlands, p. 589) and between cultivars within a species (Carroll et al., 1984; Harper and Gibson (1984) in Advances in Nitrogen Fixation Research, Veeger and Newton (eds) Nijhoff/Junk, The Hague, The Netherlands, p. 589) suggesting that host genetic factors affect nitrate-tolerance of nodulation.

Recently, Jacobsen (1984) in *Advances in Nitrogen Fixation Research*, Veeger and Newton (eds) Nijhoff/Junk, The Hague, The Netherlands, p. 597 and Jacobsen and Feenstra (1984) Plant Science Letters 33:337–344 reported the generation by mutagenesis and selection of one pea mutant that nodulates on nitrate containing medium. The mutation was described as monogenic and recessive.

It had previously been reported that extent of nodulation in legumes was affected by legume genetic factors. Gelin and Blixt, 1964, reported that the considerable variation in nodule number among pea lines that they observed was genetically controlled and that two genes (then designated No and Nod, now nod1 and nod2) were involved. Nitrate-tolerant nodulation was not reported to be associated with these genetic factors.

Although it has recently been reported (Carroll et al., 1984) that there is some variation in sensitivity of soybean cultivars to nitrate, nitrate-tolerance of nodulation has not been observed in populations of wild or domestic cultivars of soybean. Prior to the present invention, it was not known or understood that genetic manipulation of a plant could achieve a plant phenotype of nitrate-tolerant nodulation, since both plant and bacterial genes are involved in establishing effective root nodules and genetic studies involving genetic manipulation of the symbiosis has been confined to Rhizobium.

Some of the results described herein, have been reported in Carroll et al. (1985) Proc. Nat'l. Acad. Sci. U.S.A. 82:4162–4166; and Carroll et al. (1985) Plant Physiol. 78:34–40.

SUMMARY OF THE INVENTION

The present invention outlines a reproducible mutagenesis and selection procedure used to isolate 15 independent nitrate-tolerant soybean mutant lines, demonstrates the stability of the nitrate-tolerance phenotype from one generation to the next and describes the phenotypic and genetic characteristics of soybean lines having the nitrate-tolerance phenotype. Unexpectedly, some of the mutants isolated were also supernodulators. A method for mutagenesis of seeds and selection of nitrate-tolerant plants and supernodulating plants is disclosed. The mutagenesis and selection methods described herein are applicable to a wide variety of plants, in particular for mutants having an enhanced plant function, and where the desired phenotypic trait is resistance to a stress. The nitrate-tolerant nodulation phenotype is usually a recessive trait which segregates according to normal Mendelian genetic principles. Supernodulation has been found in both recessive and dominant (or semi-dominant) mutations that behave as single Mendelian traits. The mutants of the present invention represent at least four phenotype classes or groups. Mutants have been classified by complementation analysis into at least three independent genetic complementation groups. Breeding techniques can be used to introduce the phenotypes of nitrate-tolerant nodulation and supernodulation into commercial soybean cultivars. The invention is exemplified by its application to soybean (Glycine max) cv. Bragg; however, its operating principles may be applied to other cultivars of soybean, for example "Williams", and is not limited to any particular soybean cultivar, but may be applied generally to any plant varieties of the genus Glycine, whether wild, domestic or hybrids of the two. The term soybean is used herein to denote the species Glycine max and all domestic cultivars thereof.

DETAILED DESCRIPTION OF THE INVENTION

Nitrate-tolerant nodulation is here defined as the ability of the plant to form effective root nodules when grown in a support medium having a defined nitrate level, in the presence of an inoculating amount of symbiotic bacteria. Effective root nodules are those capable of carrying out nitrogen fixation. Nitrogen fixation, the process of reducing dinitrogen to biologically usable forms of nitrogen, such as ammonia, is conveniently measured by reduction of acetylene, since the enzyme catalyzing dinitrogen reduction, nitrogenase, is also capable of catalyzing acetylene reduction. Therefore, the ability to reduce acetylene is deemed equivalent to the ability to fix nitrogen and is diagnostic of the presence of active nitrogenase enzyme activity. Support medium is the term used herein to denote any material used to support the normal erect growth of a plant, including without limitations soil, sand, vermiculite and the like. Symbiotic microorganism means any organisms, most typically bacteria, of the genus Rhizobium, capable of forming an effective root nodule under appropriate conditions. A nodulating amount of a symbiotic microorganism is simply a sufficient number of such organisms distributed in the support medium to allow a wild-type or conventional cultivar to form sufficient numbers of nodules to support normal growth in an essentially nitrogen-free support medium.

Nitrate level is defined as the amount of nitrate per unit of soil volume, obtained by supplying nitrate in solution at a specified concentration, supplied to the plant under defined conditions. The nitrate level is defined in terms of the concentration of solution added because the measured soil concentration may vary due to soil drying, nitrate assimilation and other such factors. A nitrate level of 5 mM, for example, is that obtained by the equivalent of watering the plants daily in 12" deep, 10" diameter pots with 0.251 of 5 mM $KNO_3$ solution, as described herein. Such a procedure provides a relatively constant nitrate level, given the difficulties of obtaining constant concentrations of soluble material in soil.

Supernodulation is defined as the ability of the plant to form effective nodules in greater number and greater mass of nodules per plant than wild-type, by a factor of at least two-fold, when grown in a support medium in the presence of an inoculating amount of symbiotic bacteria. Supernodulating plants may be, but are not necessarily, nitrate-tolerant. The phenotype of supernodulation is observable in the absence of added nitrate.

Normal wild-type legumes and domestic cultivars of agronomically important leguminous crops, such as soybean, do not form effective root nodules in the presence of low levels of nitrate in the soil. Both nodule size and the ability to fix nitrogen are substantially reduced in soil containing 5.5 mM nitrate, when compared with controls grown in essentially nitrate-free soil in the absence of added nitrate. Residual nitrate is commonly found in soils where crop rotation is practiced and a fertilized crop, such as corn, was planted the previous season. Soybeans are commonly grown in rotation with fertilized crops. High soil nitrate levels may occur simply by the action of nitrifying bacteria or organic matter in soil. Some soils, especially those of volcanic origin, are naturally high in nitrate. Under such circumstances, effective nodulation is prevented or delayed until the residual soil nitrate is substantially depleted, a which time a lag in plant growth may be observed. The lag, which is sometimes accompanied by transient yellowing, is due to the delay in establishing nodulation. Time to maturity, susceptibility to stress, both during the lag phase and subsequently, and final crop yield are affected adversely. The value of soil inoculation during planting is decreased if the delay in establishing nodulation results in a diminished or ineffectual population of symbiotic microorganisms in the soil. The nitrate-tolerant nodulation phenotype is agronomically advantageous in preventing or reducing such adverse effects.

Nitrate leached from soils is rapidly becoming a serious pollutant of rivers and aquifers. The pollution is generated by continual applications of fertilizer to soil and leaching from soil by rain and irrigation water. Since soybeans obtain only about 70% of their total N by nitrogen fixation, reducing the dependence on added fertilizer, this helps to alleviate the pollution problem. Nitrate tolerant and supernodulating mutants reduce the need for added fertilizer.

The nirate-tolerant and supernodulation phenotypes disclosed herein are obtained by genetic modification. The term genetic modification as used herein includes any means of altering the genotype of a plant other than conventional cross-breeding. Such genetic modification means include, but are not limited to, mutagenesis, followed by selection for the desired phenotype; in vitro construction of recombinant DNA followed by transformation and selection for a desired phenotype or such other means for deleting, inactivating or altering the function of existing plant genes, or for the introduction of new genes into the plant, as may occur to those of ordinary skill in the art, following the teachings of the invention as disclosed herein.

An unusual feature of the present invention is the discovery of mutations resulting in an enhancement of plant function, e.g., the making of greater than normal numbers of effective nodules. In general, a mutation providing enhancement of plant function is an "up" mutation wherein the mutant plant produces more of a product, structure or process than wild-type plants. Since enhancements of plant function are rarely achieved by mutagenesis, the disclosed method of mutagenesis and selection will be useful for obtaining genetically modified plants having an enhanced plant function.

The genetic manipulations used herein to generate a phenotype of nitrate-tolerant nodulation were mutagenesis followed by selection. It will be understood that other genetic manipulations, such as the application of recombinant DNA techniques or the use of transposable elements, may be applied as alternative means of genetic manipulation. Seeds were mutagenised in trial experiments with ethyl methane sulfonate (EMS), sodium azide and gamma irradiation. EMS was judged preferable because it was the most efficient in generating chlorophyll-deficient mutants (chl$^-$), which are readily detected by observation of plants with yellow or white leaves. Since mutagenesis of the embryo was most likely to yield a chimeric embryo, due to the existence of more than one germ line cell in the embryo and it appeared likely that the majority of mutations would be recessive, the screening was carried out in the M2 generation. (The seeds subjected to the mutagen are termed the M1 generation, plants grown from those seeds are M1 plants, the seeds produced by the M1 plants are termed M2 seeds, the plants grown from M2 seeds are termed M2 plants, and so forth. Families of seeds are those harvested from a single plant. Therefore, an M2 family of seeds includes all the descendants of a single mutagenised seed.)

Having chosen EMS mutagenesis as the preferred means of genetic manipulation, large scale mutagenesis and selection was done. M1 seeds were mutagenised with EMS in 2 batches, one at 0.44% (v/v) for 4 hours exposure, or at 0.5% (v/v) for 6 hours exposure, and then planted. Selection for nitrate-tolerant nodulation was not carried out with the M1 plants; however, survival rates and frequency of appearance of chl$^-$ mutations was noted, in order to get a general estimate of mutation frequency and lethality of the mutagenesis. At maturity, M2 seed families were collected and kept separately, harvesting the M2 seeds in bulk.

Grouping the individual M2 families has several advantages in the selection process. First, it is possible to recognize which mutants arose from the same mutation event. Second, if a given selected variant were to be lost before it produced seed, it was possible to go back to the designated family and reisolate the remaining mutant individuals (siblings) from the family.

For selection of nitrate-tolerant mutants, 10–12 seeds from each family were planted at 2 cm depth in pots using washed river sand as the support medium. The plants were cultured in the presence of nitrate and a commercial soil inoculant (USDA 136) for 5–7 weeks, then carefully removed from the sand and visually screened for extent of nodulation. Pots were initially watered 3 times per week, but this was increased to daily waterings as the demand increased with growth. Out of 2500 M2 families, by screening more than 25,000 individual plants in the manner described, 15 nitrate-tolerant mutants were obtained. (Table 1)

Figure 1:
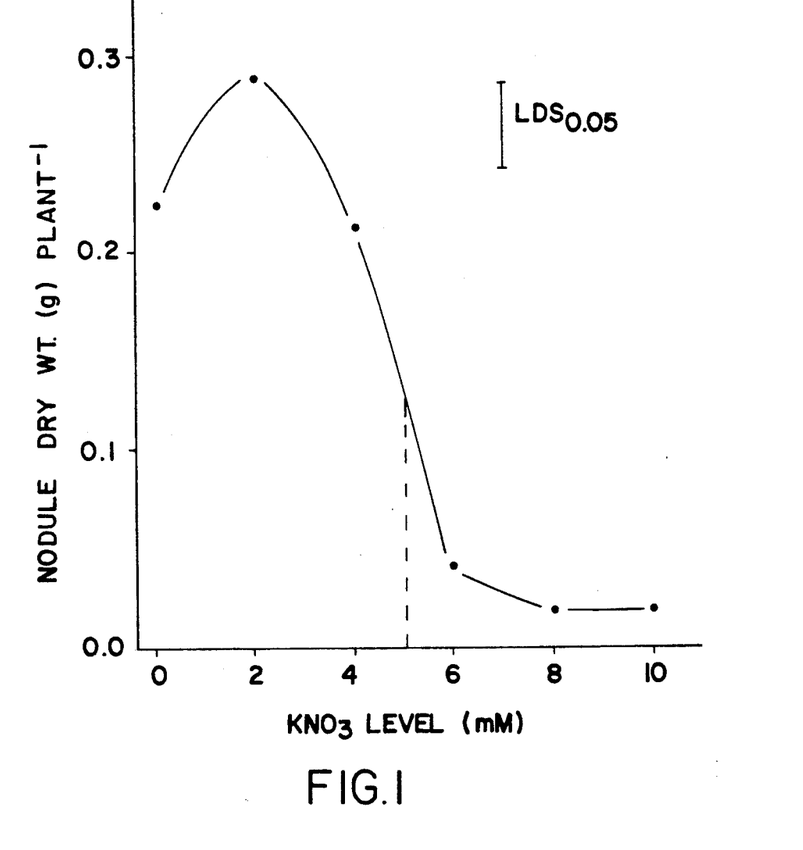
FIG. 1 is a graph showing the effect of soil nitrate level on nodulation of wild-type cultivar Bragg. Specifically, nodule dry weight as a function of $KNO_3$ concentration is shown.

The concentration of nitrate used for selection was determined by preliminary experiments with the parent cultivar, Bragg. FIG. 1 shows the results obtained, measuring nodule fresh weight as a function of $KNO_3$ level during growth. At about 5–6 mM $KNO_3$, nodule size was drastically reduced and a small increase in nitrate tolerance by an individual plant would be manifest in a substantially increased nodule fresh weight. The selected variants showed significantly increased nodulation in the presence of 5 mM $KNO_3$ compared to wild-type siblings and the parent cultivar. Since the selection process was time consuming and laborious, only those individuals displaying obviously increased nodulation upon visual inspection were selected. Many more variants having marginally increased nodulation were also observed. It is possible that further analysis, for example by measurement of acetylene reduction, would reveal the existence of additional nitrate-tolerant variants, since an increase in nitrogen-fixing capacity or efficiency of individual nodules would produce a phenotype of nitrate tolerance. Since these mutants have not been characterized to date, the invention is exemplified by characterization of the mutants that displayed significantly increased nodulation. Nodule numbers per plant for selected mutants and their wild-type siblings are shown in Table 2. The wild-type siblings of nitrate-tolerant mutants had a nodule number not significantly different from that of Bragg. Nodule number for the mutants ranged from 16 nodules per plant for nts65 up to 370 nodules per plant for nts2062. In the case of nts2062, the nodule number as a function of plant mass was 10 times greater than in the wild-type (Bragg) grown under identical conditions, i.e., 5 mM $KNO_3$. Comparison of the mutant grown on nitrate to the wild-type grown in the absence of nitrate was equally striking: nts2062 grown in the presence of 5 mM $KNO_3$, which causes a 56% reduction in nodules per plant mass in the wild-type has 4.5 times as many nodules as does the wild-type grown in the absence of nitrate, conditions under which the wild-type is presumably forming its maximum number of nodules. Similarly, measurements of nodule mass showed that nts2062 plants grown on nitrate have 12 times the nodule mass as wild-type grown on nitrate, and 3.5 times the nodule mass of wild-type plants grown in the absence of nitrate.

Figure 2:
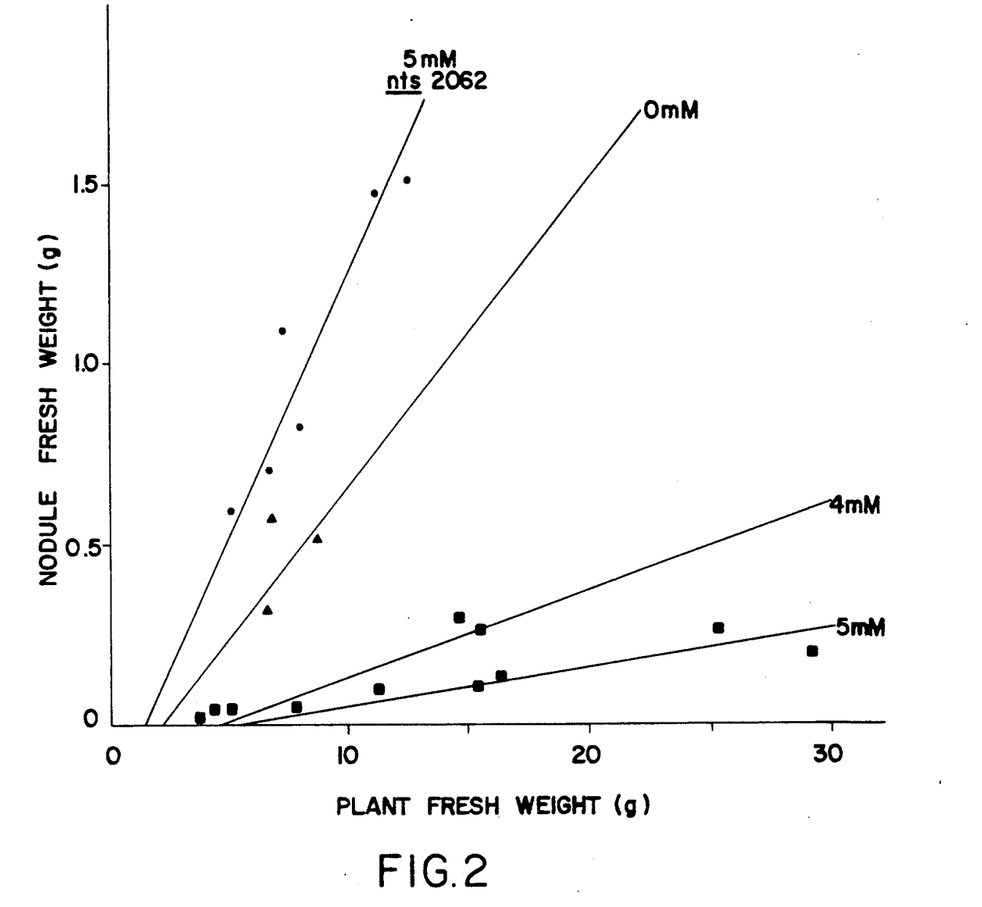
FIG. 2 is a graph showing the effect of soil nitrate level on nodule fresh weight per unit plant mass. A comparison is made between wild type cultivar Bragg at 0, 4 and 6 mM nitrate and nts mutant 2062 at 5 mM nitrate.

FIG. 2 shows nodule fresh weight as a function of plant size (fresh weight) for nts2062 grown in 5 mM $KNO_3$ and Bragg grown in 0, 4 and 6 mM $KNO_3$. The data demonstrate that nodule fresh weight per plant mass is greater in nts2062 cultured in 5 mM $KNO_3$ than wild-type Bragg grown in the absence of nitrate. In contrast to nts2062, nts2282 cultured on 5 mM $KNO_3$ displays a nodule fresh weight per plant size approximately equal to that of the wild-type Bragg cultured in the absence of nitrate. Furthermore, wild-type siblings of nts2062 and nts2282 cultured on 5 mM KNO$_3$ approximate the values obtained for the parent cultivar, Bragg, cultured on 4–6 mM KNO$_3$.

Figure 3:
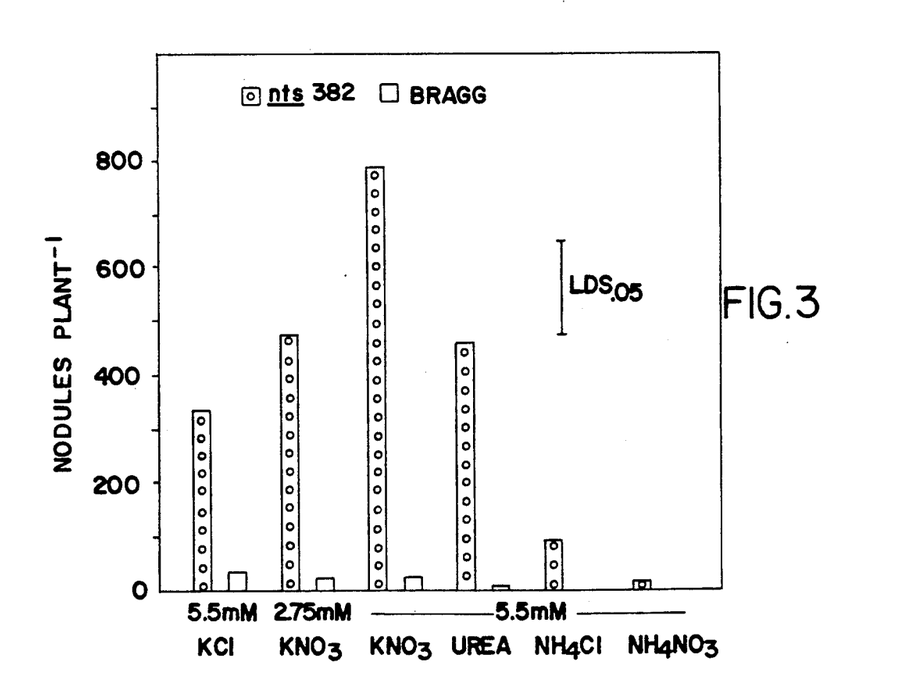
FIG. 3 is a graph comparing nodulation of the wild type Bragg cultivar with nts mutant 382 under a variety of growth conditions. The number of nodules per plant is compared at different levels of nitrate (0, 2.75 and 5.5 mM) and in the presence of other nitrogen-containing compounds.

High nodule numbers were also observed for nts382. FIG. 3 shows a comparison of nts382 with Bragg under a variety of growth conditions. As the nitrate concentration increased, the number of nodules per plant actually increased with nts382, while for Bragg the number decreased. The effect of other nitrogen-containing compounds in the support medium is also shown. The presence of ammonium at 5.5 mM reduced the number of nodules per plant; however, the mutant continued to form significantly more nodules than the wild-type. The effect of ammonium may be wholly or partially accounted for by pH changes in roots that have taken up large amounts of ammonium ion. When the number of nodules per gram of plant fresh weight was measured, the variety nts382 remained constant up to 5 mM KNO$_3$, whereas the wild-type decreased. The presence of urea and ammonium decreased the nodule number for both the mutant and the wild-type; however, the mutant was able to form nodules under conditions where the wild-type was not.

Figure 4:
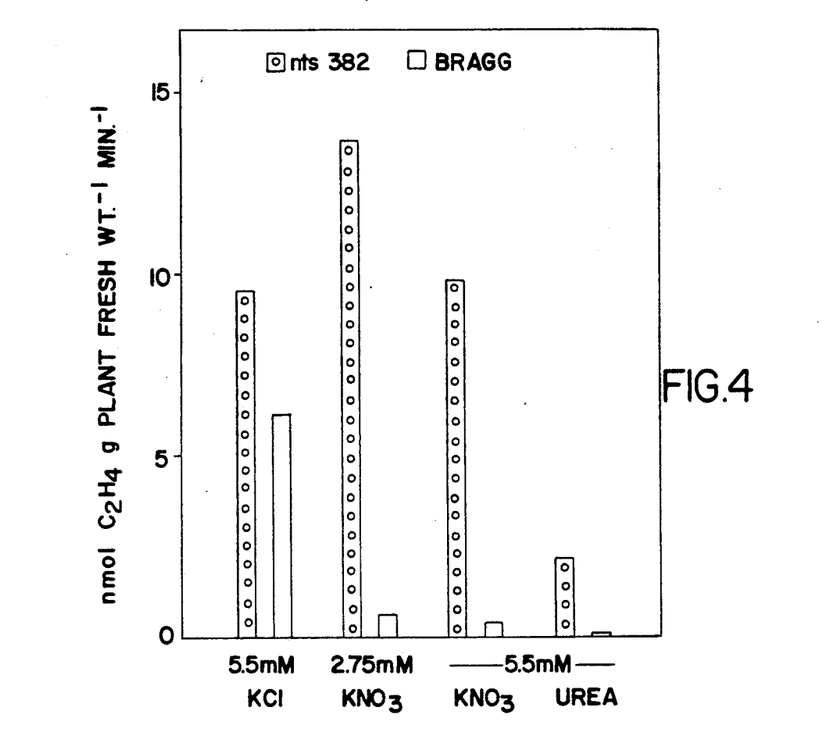
FIG. 4 is a graph comparing acetylene reduction rates, i.e., nitrogenase activity (nmoles $C_2H_4.g$ plant fresh weight$^{-1}$.min$^{-1}$) of wild-type Bragg with nts382 at 6 weeks after plating as a function of nitrate level.

Acetylene reduction assay (Hardy et al. (1968) Plant Physiol. 43:1185–1207) was used to estimate nitrogen fixation. Conversion of acetylene to ethylene was measured by gas chromatography. Intact plants were placed in 1040 ml airtight jars in a 6% (v/v) acetylene atmosphere, incubated over a 40 minute period. Subsequently, the seedlings were replanted and grown to maturity. In some experiments, detached nodules from mutants or wild-type were assayed instead of whole plants. FIG. 4 shows a comparison of acetylene reduction rates between wild-type and nts2062 at 6 weeks after planting. In wild-type soybeans cultured in the absence of nitrate, nitrogenase activity per plant and per plant mass was about 16 times higher than wild-type grown on 5 mM KNO$_3$. In comparison, nts2062 plants cultured on 5 mM KNO$_3$ had approximately 10 times the activity of wild-type grown under identical conditions. At harvest, 6 weeks after planting, the nitrogenase activity of nts2062 plants grown on nitrate was about 55% of that of wild-type grown in the absence of nitrate. Plants of mutant line nts2264 had 4 times the nitrogenase activity of wild-type siblings. Expressing the data for nts2264 per plant fresh weight the activity of the variants was about 6 times that of the wild-type, which, in part, reflected the smaller size of the mutants. Similar values were obtained from mutants nts382 and nts1116. Data comparing nts382 and Bragg are shown in FIG. 4. For the wild-type, nitrogenase activity was sharply reduced at a KNO$_3$ level of 2.75 mM and reduced even more at 5.5 mM KNO$_3$. In contrast, nitrogenase activity of nts382 remained constant or increased with increasing KNO$_3$ levels up to 5.5 mM. Also noteworthy is the observation that, although urea at 5.5 mM (total N 11 mM) the nitrogenase activity of both wild-type and mutant were reduced. However, nts382 retained many times greater nitrogenase activity than did the wild-type.

Figure 5A:
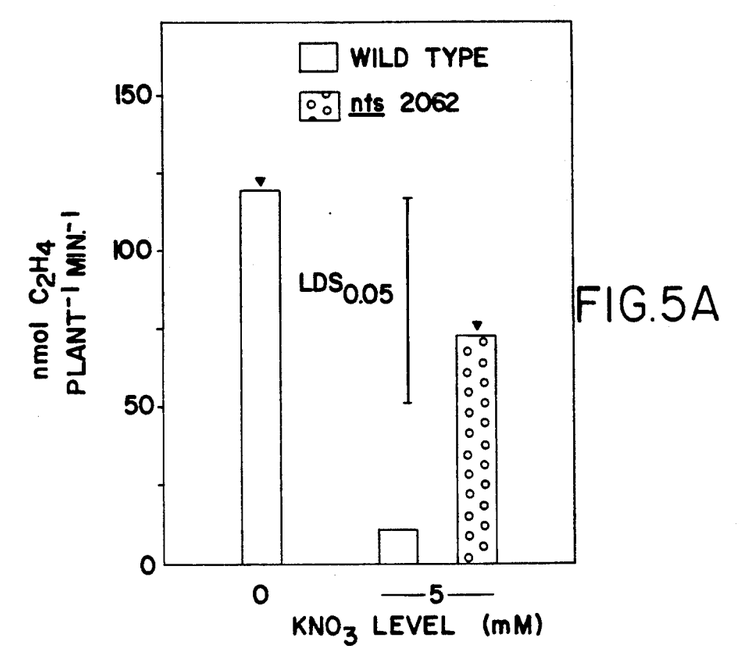
FIG. 5 is a graph comparing nitrogenase activity per gram of fresh nodule weight (nmoles $C_2H_4.g$ plant fresh weight$^{-1}$.min$^{-1}$) of wild-type Bragg with nts2062 as a function of nitrate level.
Figure 5B:
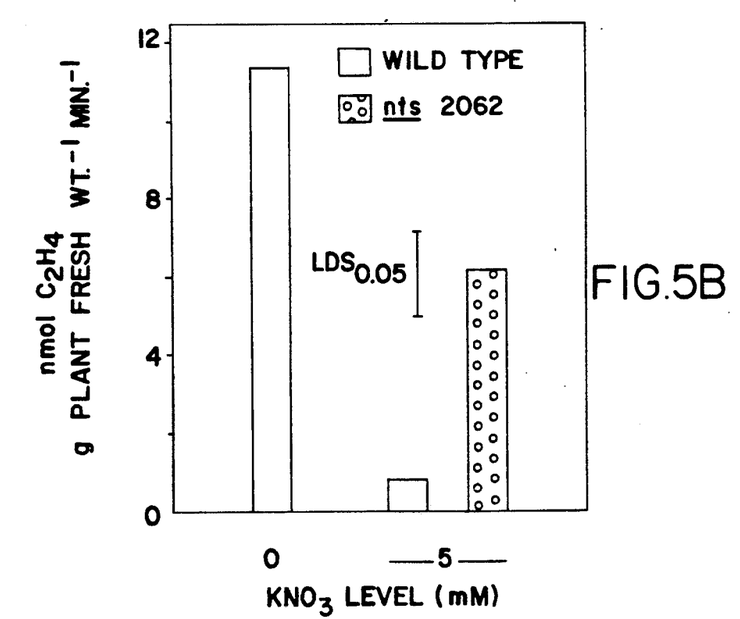

FIG. 5 shows the nitrogenase activity per gram of nodule fresh weight (specific nitrogenase activity) in nts2062. Activity was the same as for the wild-type cultured under identical conditions. Specific nitrogenase activity of both nts2062 and wild-type cultured on 5 mM KNO$_3$ was about 20% of that of the wild-type grown under nitrogen-free conditions. In separate experiments, cultures of two other high-nodulating lines, nts382 and nts1007, showed a similar trend. Specific nitrogenase activity of Bragg, nts382 and nts1007 grown on nitrate were not significantly different from one another.

Plants displaying the nitrate-tolerant phenotype were generally smaller than wild-type siblings and the parent cultivar, Bragg. For example, mutants nts246 and nts1007 were significantly shorter and had significantly smaller leaf area than the respective wild-type siblings. Data is shown in Table 3. Composite data for several nts lines compared with their wild-type siblings, chosen as a better control for this purpose than Bragg wild-type which had not undergone mutagenesis, shows that at approximately 6 weeks after planting, the mutants had grown to about 84% the height and had about 80% the leaf area of the wild-type siblings. The same trend was reflected in measurements of plant fresh weight, the mutants averaging somewhat less in weight than the wild-type siblings, although for some strains, e.g., nts2282, the difference was not significant.

The rate of nodulation during growth was studied, comparing nts382 and wild-type Bragg, both inoculated with Rhizobium USDA 110, grown in sand gravel with daily waterings of nutrient media plus a supplement, either 5.5 mM KNO$_3$ or 5.5 mM KCl. At intervals, a number of test plants was removed from pots to determine the number of nodules per plant. Results are shown in Table 4. Nodulation rates of nts382 were consistently higher throughout the growth of the plants than were the wild-type rates, both in the presence and absence of nitrate. The results also demonstrate that the observed phenotypes are not related to strain specificity of the inoculating Rhizobrium, since both USDA 110 and USDA 136 nodulated nts382 with substantially similar results.

A comparison of nts382 with wild-type Bragg was carried out at 0, 2.75 and 5.5 mM KNO$_3$ measuring nodule number per plant, nodule fresh weight as a percent of root fresh weight, and nitrogen fixation ability as rate of acetylene reduction per gram of plant fresh weight. The results are shown in Table 5. In addition to the strikingly higher nodule numbers per plant and greater nodule weight per plant, characteristic of the supernodulation phenotype, the ability of nts382 to fix nitrogen was greater than the wild-type at all nitrate levels studied. All of the nts mutants studied had a higher nitrogenase activity per plant and per plant fresh weight than the wild-type siblings when cultured on nitrate. In contrast, in the absence of nitrate, nitrogenase activity per plant at time of harvest was greater in wild-type than for nts2062 grown on nitrate. The specific nitrogenase activity of wild-type and nts2062 cultured on nitrate was identical, and in both cases it was 20% of the activity of wild-type grown under nitrogen-free conditions. A similar trend was shown in measurements with detached nodules of nts382 and nts1007 cultured on 5 mM KNO$_3$, compared with wild-type grown in the presence and absence of nitrate. A more detailed analysis of nts382 has shown that it behaves similarly to nts2062. The results also suggest that these nts mutants are capable of using both endogenously fixed nitrogen and exogenous nitrate, a matter of considerable agronomic significance.

The genetics of the nitrate-tolerant mutants suggests that most but not all of them behave as Mendelian recessives. The frequency of appearance of mutant in the M2 generation, where recessive mutants must be homozygous to be detectable, is a function not only of the normal Mendelian frequency of appearance of homozygous recessives (3:1), but also of the genetically effective cell number (GECN). The GECN is a measure of the number of germline cells contained within an embryo, any one of which may give rise to the mature plant, assuming each of them has an equal probability of doing so. For example, if GECN=1, the M2 segregation ratio will be 3:1; if it is 2, the ratio will be 7:1, and if GECN=3, the segregation ratio will be 11:1, and so forth. Judging by the segregation ratios observed for the recessive nitrate-tolerant mutants, the GECN for soybean is estimated at between 3 and 5. It follows that M2 segregation ratios significantly lower than 11:1 may indicate that the mutant is not recessive. Further evidence of recessiveness is provided by measuring segregation ratios in M3 plants. If a mutant is a true recessive, its appearance in the M2 generation will be manifest only in the homozygous state and its M3 progeny should not segregate. On the other hand, if there is segregation in the M3 generation, it may be presumed that the mutant is dominant or semi-dominant. For example, in the case of nts246, there were two nitrate-tolerant plants observed in the M2 family of 10 members. Furthermore, in the M3 generation, one of the two isolates yielded wild-type segregants, indicating it was heterozygous in the M2. Therefore, nts246, uniquely among the 15 nitrate-tolerant strains isolated to date, represents a dominant, or semi-dominant, mutation.

On the basis of their genetic behavior and on the characteristics of nodulation in the presence of nitrate, the nitrate-tolerant soybean varieties isolated to date can be classified into four phenotype groups (see Table 1). Group 1, represented by nts246 and nts733, is characterized as dominant or semi-dominant, relative to wild-type, and behaves as a supernodulator. (Supernodulation is defined as an increase of at least two-fold in nodule number and nodule mass over wild-type, when comparing mutant and wild-type grown in the absence of added nitrate.) Group 2 is represented by nts strains 382, 2062, 501 and 1007. Mutants in this group are recessive, relative to wild-type, have supernodulation, the rate of nitrogen fixation per plant is equal to or greater than wild-type in the presence or absence of nitrate and the specific activity (expressed per mg bacteroid protein) of the nitrogenase is essentially equal to wild-type in the absence of nitrate. Specific activity per nodule mass is lower in these mutants than Bragg due to a decreased amount of infected tissue per nodule. Group 3 is represented by nts65. Group 3 mutants are recessive, display normal nodule number in the presence of 5 mM nitrate, but increased nodule size, i.e., nodule mass per plant is greater than wild-type. Group 4 is represented by strains nts97, nts1116 and nts225. Mutants are recessive to wild-type, but interestingly may be dominant (or co-dominant) to nts382. Nodule number and mass in plants grown on 5 mM nitrate range from equal to or greater than wild-type grown in the absence of nitrate and is thus characterized as intermediate (a hypernodulator). However, in addition the nodules are found more frequently on the peripheral roots and less frequently on the tap roots, suggesting that in these varieties nodulation may be occurring late in plant growth as an adaptive response to high nitrate. The four phenotype classes can each represent different genetic complementation groups using genetic complementation analysis (see Example 3). Crossing studies have clearly distinguished three different complementation groups of nts mutants (see Table 1). Three class 2 mutants: nts382, nts1007 and nts501 have been assigned to complementation group A. Both class 1 mutants nts246 and nts733 have been assigned to complementation group C. One class 4 mutant has been assigned to complementation group B. A complementation group defines a genetic unit. Mutations are characterized as belonging to a particular complementation group by their inability to complement when tested in pairwise combinations in trans.

The finding that some mutants had the phenotype of supernodulation was unexpected. Supernodulation is distinguished from nitrate tolerance in that the former is manifested in the absence of added nitrate. Therefore, some but not all supernodulators are nitrate tolerant. Had selection been carried out for supernodulation, by screening M2 plants in the absence of nitrate, supernodulating strains that lacked nitrate tolerance could have been isolated.

The phenotype of nitrate tolerant nodulation is distinguishable from an inability to utilize nitrate in that the latter are simply unresponsive or less responsive to the effects of nitrate than wild-type, depending on the leakiness of the mutant. If one were to compare nodule fresh weight as a function of plant fresh weight in such a mutant on a plot of the type shown in FIG. 2, one would expect nitrate utilization deficient mutants to fall somewhere within the range of behaviors for wild-type, between 0 mM and 6 mM $KNO_3$. That is, individual plants of such a mutant line would plot on FIG. 2 between the fitted lines for Bragg (or other wild-type progenitor) cultured on the various nitrate levels. The exact location between these fitted lines would depend on whether or not the nitrate assimilation mutant was leaky. This was not the case for nts2062 and other supernodulating mutants, which produced greater nodule mass than wild-type when grown in the absence of nitrate. The strain nts382 has also been shown to behave as a typical supernodulator in forming greater nodule fresh weight per gram of plant than wild-type at all nitrate levels. Furthermore, direct experiments have shown that nts382 can assimilate nitrate. Therefore, the phenotypes of nitrate tolerant nodulation and supernodulation are distinguishable from deficiencies in nitrate utilization or nitrate assimilation.

Specific aspects and features of the present invention are further illustrated by the following examples.

EXAMPLE 1

EMS Mutagenesis of Plant Seeds

Since EMS is highly mutagenic even in the volatile (gaseous) form, all procedures were carried out using a fume hood, neoprene gloves and vapor traps. EMS mutagenesis requires an actively respiring embryo. This is best achieved by imbibing seeds in water bubbled with air or under running tap water prior to EMS exposure. The following is a soybean technique and may be modified for other plant seeds.

Only seeds having high viability as determined by pre-experiments were used. Seeds (5,000 as a minimum) were counted and packaged in plastic wire-netting envelopes (1,000 seeds per bag, fly-screen plastic netting works very well).

The seed bags were placed in a container and flushed with tap water (28 C) through the seeds for 12 hours.

Seeds were then transferred to 0.1M $KH_2PO_4$ pH 6.0 (1 liter/1,000 seeds) and ethyl methane sulfonate (EMS)

was added to give a final concentration of 0.5% (v/v). The solution was bubbled with air (to effect agitation and aeration) and the fumes were removed through a vapor trap. The vapor trap solution was 2% potassium hydroxide (w/v) plus 10% (w/v) sodium thiosulphate. *All the steps involving handling of EMS were carried out in a fumehood.*

After six hours exposure to EMS, the aeration was stopped and the mutagen solution was decanted through a hose connecting a tap on the bottom of the mutagenesis vessel to a similar vessel for inactivation. The inactivation vessel already had a freshly prepared concentrated KOH—sodium thiosulphate solution in it. See "EMS inactivation solution", infra. The tap was closed and the mutagenesis chamber was filled with water. Air was bubbled through the chamber to effect agitation for a few minutes, then the rinse was decanted into the inactivation vessel. The seeds (still in rinsed mutagenesis vessel) were washed for 3 hours, then the seed bags were removed, using fishing line attached to assist removal, and washed for a further 1 hour under the tap. The inactivation solution was agitated with bubbling air for several hours, then decanted down the fumehood sink with copious amounts of water.

Seeds were removed from seed envelopes and planted immediately. Those handling the seeds should do so only where it is well ventilated and should wear protective gloves. Two planting procedures were used: (a) field planting: directly into the furrow followed by quick hand watering; (b) pot plantings: 10 inch diameter pots 1 foot deep (filled with sand plus slow release fertilizer) were planted with 10-14 soybean seeds per pot. Seeds were spread onto the surface of the pre-filled pots, then covered by about 2 cm of additional sand. Attempts at drying back the seeds with a hair dryer to permit transport between the lab and field site resulted in increased seed loss.

The M1 generation was grown and compared for vigor with unmutagenised control plants. Survival numbers were scored to get a general estimate of viability and mutagenicity was estimated by noting the frequency of sectoring of chlorophyll deficiencies. Prospective chimeric plants were labeled for future analysis.

Seeds were allowed to mature completely. Seeds of the M2 generation were collected from each plant and bagged separately. Separate collection of M2 families allowed the determination of GECN (genetically effective cell number) and more rapid screening. For example, it is certain that any mutant isolated in the M2 screen is separate from any other. Also on those occasions when one loses a selected plant, it then is possible to go back to the family and select a sibling.

Two separate EMS mutagenic treatments were performed, with a total of 400,000 to 500,000 seeds mutagenized. A total of 15 independent mutants (Table 1) were isolated in these mutageneses.

EMS Inactivation Solution

Dissolve 8 g KOH in 400 ml H2O (this stabilizes thiosulphate). Add 40 g sodium thiosulphate and dissolve. Submerge all articles for 24 hours, then discard in running water inside of fume hood (an odd smell will still persist). Use this inactivating solution also in the vapor trap. Although the EMS was presumed to be substantially inactivated by the foregoing solution, no measurements of residual EMS concentration were made.

EXAMPLE 2

Screening for Nitrate-Tolerant Mutants

M2 families were planted into sand pots (1 family per pot), inoculated with commercial part inoculum, and grown for 4-6 weeks. Plants were watered with a standard nutrient solution containing 5 mM $KNO_3$. To ensure a constant nitrate concentration level, the pots (10 inches diameter, 1 foot depth) were flushed with about 1.4 l of solution at each watering. Pots were initially watered 3 times per week, and more frequently as demand increased with growth. All plants were carefully removed from the sand and visually screened for extent of nodulation and for segregation (depends on GECN); i.e., if GECN=1, 3:1 mutant, if GECN=2, 7:1, if GECN=3, 11:1; if GECN=4, 15:1 (assuming recessive mutations). The M2 families were also screened for chl— (chlorophyll deficiency). This parameter helps to evaluate the GECN and the mutagenic efficiency.

Selection for the supernodulation phenotype is conducted in the same fashion, except that $KNO_3$ is not included in the watering solution.

Table 1 lists fifteen independent nts mutant soybean lines resulting from the above mutagenesis/selection method. A phenotypic classification of each line is provided. Genetic classification is also given, where possible, based on results of complementation analysis (Example 3).

EXAMPLE 3

Mutant Complementation Analysis

Conventional genetic complementation analysis was used to classify nts mutant soybean varieties into genetic complementation groups.

Verified, true breeding nts mutant soybean plants were brought to flowering. Prior to anthesis, specific flowers were selected, opened with sterile dissection forceps and emasculated. Donor pollen was taken from relevant nts mutant and wild type soybean plants. Mature pollen was obtained from anthers and transferred to the emasculated flower using a camel-hair brush. Cross fertilized flowers were carefully labelled with source of pollen. Individual plants, having several flowers, could thus be used for several crosses. Control, self-fertilization and reciprocal crosses were also included. Plants containing fertilized flowers were grown to maturity and individual pods (1-3 seeds/pod) were harvested and F1 progeny seeds were planted out in sand/vermiculite mix watered with 5 mM $NO_3$. F1 plants were scored for nts phenotype 4-6 weeks after inoculation with *B. japonicum* USDA110. Crosses of mutants in different complementation group score as wild-type phenotype (i.e., the mutations complement). As is known in the art, lack of complementation (i.e., non-wild-type phenotype displayed by progeny of a cross) may also result from accidental self-fertilization prior to emasculation. In order to be sure that two mutants do not complement, it is necessary to make a large number of crosses in order to exclude any accidental self-fertilization events. Alternatively a dominant genetic marker carried by the pollen donor plant can be used as an internal label for the source of pollen.

EXAMPLE 4

Soybean Breeding Method

Nitrate-tolerant nodulation soybean varieties and supernodulation soybean varieties can be generated using commercial wild-type cultivars as the wild-type starting material. Such wild-type varieties as Bragg and Williams have been described by way of example; however, it will be apparent to those of ordinary skill in the art that other commercial cultivars may be employed as progenitor strains. Once a variety with desired phenotypic traits has been obtained by the above-described mutagenesis and selection, it may be preferred to transfer the trait to other commercial cultivars by conventional plant breeding methods to achieve a new variety combining the desired phenotype (nitrate tolerance, supernodulation) with other valuable agronomic traits.

The desired commercial cultivar is crossed by conventional plant hybridization with a mutant variety having the phenotype of nitrate-tolerant nodulation or of supernodulation. Whether the mutant parent is preferably used as the male parent or the female parent is a matter which may be readily determined by making test crosses, or by comparing the results of mass crossings made both ways. Where the mutant is recessive, the F1 progeny plants will display wild-type nodulation characteristics. The F1 hybrids are selfed to produce F2 hybrids in which the recessive phenotype reappears in a portion of the F2 plants. F2 hybrid parents are then selected, to retain those having the desired phenotype, either nitrate-tolerant nodulation or supernodulation, using selection means appropriate and specific for the desired phenotype, as described in Example 2. The F2 plants are then backcrossed with the parental commercial cultivar in a recurrent manner, repeating the steps just described in selecting a strain which combines the desired agronomic traits of the commercial cultivar parent with the nitrate-tolerance or supernodulation phenotype, as desired. Selections in all cases are carried out as previously described for the mutagenesis procedure.

It will be understood that the number of possible biochemical and physiological traits associated with nitrate tolerance or supernodulation is not exhausted by the present data disclosed herein. Therefore, it may be possible to employ other selection means, less time-consuming or more specifically associated with a given class of nitrate tolerant or supernodulation mutants, and that such selection or detection means may be employed as equivalents to the techniques disclosed herein. Similarly, further studies may result in the elucidation of additional complementation groups. All such additional information, deemed cumulative and supplementary to the teachings herein, is deemed to fall within the scope of the claims.

Seeds of *Glycine max* cv. Bragg nts382 originally placed on deposit at Agrigenetics Advanced Science Company, 5649 East Buckeye Road, Madison, Wis. 53716, and seeds of nts65, nts1116 and nts246 were placed on deposit with an independent depository, In Vitro International, Inc. preesent address: 611 P Hammonds Ferry Road, Linthicum, Md. 21090. The deposit was given accession No. IVI-10111. The seed deposit originally made with In vitro International, Inc. has subsequently been transferred to the American Type Culture Collection (ATCC), which received the deposit on Jun. 20, 1991. The seeds have been given ATCC deposit numbers as follows: nts382 is ATCC 75150; nts65 is ATCC 75151; nts1116 is ATCC 75152; and nts246 is ATCC 75153. Access to the material on deposit will be available during the pending period of the patent application to one determined by the Commissioner to be entitled thereto under 37 C.F.R. 1.14 and 35 USC 122.

Seeds of nts382, nts65, nts1116 and nts246 were chosen for deposit, as representative of the four mutant phenotype classes of nitrate tolerant nodulation and supernodulation that have been identified. Further, nts382 has been classified into complementation group A, nts1116 into group B and nts246 into group C. This deposit is made to further exemplify the invention. It is not intended as in any way limiting the scope of the invention.

TABLE 1 nts Mutant Soybean Lines

| Line | Complementation Group | Phenotype |
| --- | --- | --- |
| nts382 | A | Group 2; recessive[1]; supernodulator |
| nts2062 | NA[3] | Group 2; recessive[1]; supernodulator; rate of nitrogen fixation/plant less than or equal to wild type in presence of nitrate |
| nts2282 | NA[3] | |
| nts246 | C | Group 1; dominant or semi-dominant[1]; supernodulator |
| nts65 | NE[4] | Group 3; recessive[1]; normal nodule number in presence of nitrate; increased nodule size in presence of nitrate |
| nts1116 | B | Group 4; recessive[1], dominant or co-dominant[2]; hypernodulator |
| nts2264 | NA[3] | |
| nts1007 | A | Group 2; recessive[1]; supernodulator; rate of nitrogen fixation/plant less than or equal to wild type in presence of nitrate |
| nts97 | NA[3] | Group 4; recessive[1], dominant or co-dominant[2]; hypernodulator |
| nts183[5] | NA[3] | |
| nts225 | NA[3] | Group 4; recessive[1], dominant or co-dominant[2]; hypernodulator |
| nts501 | A | Group 2; recessive[1]; supernodulator; rate of nitrogen fixation/plant less than or equal to wild type in presence of nitrate |
| nts733 | C | Group 1; dominant or semi-dominant[1]; supernodulator |
| nts739 | NA[3] | |
| nts761 | NA[3] | |

[1]With respect to wild-type
[2]With respect to nts382
[3]Not assigned
[4]Not yet established; may represent a fourth complementation group (D).
[5]nts183 carries an additional mutation conferring male-sterility which results in empty pods

TABLE 2

Nodule number for Bragg, nts mutants/variants and wildtype siblings cultured on 5 mM $KNO_3$ for 5-7 weeks. Unless noted, the data is for $M_2$ plants.

| Selected family | nodule number plant$^{-1}$ ($\pm$S.E.) | |
| --- | --- | --- |
| | Mutants/variants | Wildtype siblings |
| Bragg[1] | — | 19 ± 11 |
| 382 | 146 ± 24 | 26 ± 12 |
| 1007 | 179 ± 12 | 13 ± 12 |
| 1116[2] | 79 ± 20 | — |
| 246[2] | 115 ± 15 | 8 ± 17 |
| 733 | 213 ± 26 | 18 ± 14 |

TABLE 2-continued

Nodule number for Bragg, nts mutants/variants and wildtype siblings cultured on 5 mM KNO$_3$ for 5–7 weeks. Unless noted, the data is for M$_2$ plants.

| Selected family | nodule number plant$^{-1}$ (±S.E.) | |
|---|---|---|
| | Mutants/variants | Wildtype siblings |
| 183 | 269 ± 21 | 19 ± 17 |
| 65[3] | 16 | 9 ± 17 |
| 97[4] | 120 | 32 ± 21 |
| 225[4] | 75 | 17 ± 12 |
| 501[4] | 251 | 19 ± 17 |
| 206[2] | 370 ± 26 | 38 ± 12 |

[1] parent cultivar
[2] data from M$_3$ plants
[3] two nts plants, both had 16 nodules
[4] data for nts mutants/variants from 1 plant only

TABLE 3

| Selected family | Phenotype | Height (cm) ± S.E. | Leaf area ± S.E. |
|---|---|---|---|
| 246 | mutants | 22.6 ± 2.4 | 162 ± 15 |
| | siblings | 35.5 ± 2.5 | 227 ± 10 |
| | ratio (m/s) | 0.64 | 0.71 |
| 1007 | mutants | 36.4 ± 2.0 | 158 ± 12 |
| | siblings | 36.9 ± 1.6 | 206 ± 13 |
| | ratio (m/s) | 0.78 | 0.77 |
| 382 | mutants | 43.5 ± 6.0 | 166 ± 16 |
| | siblings | 52.7 ± 1.8 | 281 ± 3 |
| | ratio (m/s) | 0.83* | 0.59 |

*not significantly different

TABLE 4

Nodulation of nts382 versus Bragg wild-type in the presence of NO$_3$[1]

| | Nodule per plant after (±S.D.) | | | |
|---|---|---|---|---|
| | Day 9 | Day 15 | Day 22 | Day 29 |
| Bragg (+KCl) | 6 ± 4 | 22 ± 10 | 37 ± 14 | 39 ± 6 |
| nts382 (+KCl) | 54 ± 17 | 103 ± 35 | 294 ± 70 | 320 ± 48 |
| Bragg (+5.5 mM KNO$_3$) | 5 ± 2 | 9 ± 4 | 19 ± 8 | 22 ± 11 |
| nts382 (+5.5 mM KNO$_3$) | 63 ± 19 | 380 ± 43 | 483 ± 114 | 693 ± 142 |

[1] inoculated with USDA 110, grown in sand gravel with daily waterings of nutrient media plus supplement (5.5 mM KNO$_3$ or KCl)

TABLE 5

Summary of nts382 mutant performance[1]

| Line | N-source | Nodule number per plant | Nodule fresh weight (% of root fresh weight) | Nitrogen fixation ability (nmol C$_2$H$_4$ min$^{-1}$ g plant fresh weight) |
|---|---|---|---|---|
| Bragg | 0 mM (KCl control) | 37 | 8 | 6.12 |
| nts382 | 0 mM (KCl control) | 339 | 49 | 9.50 |
| Bragg | 2.75 mM KNO$_3$ | 27 | 2 | 0.60 |
| nts382 | 2.75 mM KNO$_3$ | 474 | 60 | 13.54 |
| Bragg | 5.5 mM KNO$_3$ | 25 | 1 | 0.33 |
| nts382 | 5.5 mM KNO$_3$ | 783 | 69 | 9.73 |

[1] Grown in sand, inoculated with CB 1809 (=USDA 136); flushed daily and harvested at 4 weeks.

We claim:

1. A mutant soybean plant having nitrate tolerant nodulation as a distinguishing phenotype wherein the mutation which conveys the nitrate-tolerant nodulation phenotype of said mutant is stable from one generation to the next and wherein said phenotype is observable in said mutant as:

(a) an increase in nitrogen-fixing capacity or efficiency of individual nodules compared to wild-type when said mutant and wild-type are grown in a support medium having a nitrate level of about 5–6 mM;

(b) nodule mass per plant greater than wild-type and a normal nodule number compared to wild-type, when said mutant and wild-type are grown in the presence of 5 mM nitrate; or (c) nodule number and nodule mass in mutant plants on 5 mM nitrate ranging from equal to or greater wild-type grown in the absence of nitrate.

2. The mutant soybean plant of claim 1 produced by mutation of *Glycine max* cv. Bragg.

3. The mutant soybean plant of claim 1 produced by mutation of *Glycine max* cv. Williams.

4. The mutant soybean plant of claim 1 comprising a mutant variety which can be classified into the same phenotype group as a mutant variety selected from the group consisting of nts382, nts2062, nts2282, nts246, nts65, nts1116, nts2264, nts1007, nts97, nts183, nts225, nts501, nts733, nts739 and nts761.

5. The mutant soybean of claim 1 comprising a mutant variety which can be classified into the same phenotype group as a mutant variety selected from the group consisting of nts382, nts246, nts1116 and nts65.

6. The mutant soybean of claim 1 comprising a mutant variety which can be classified into the same genetic complementation group as a mutant variety selected from the group consisting of nts382, nts246 and nts1116.

7. The mutant soybean of claim 1 that is a mutant variety selected from the group consisting of nts382, nts246, nts1116 and nts65.

8. A mutant soybean plant having a phenotype of supernodulation.

9. The mutant soybean plant of claim 8 wherein said supernodulation phenotype is conveyed by a dominant or semi-dominant mutation.

10. The mutant soybean plant of claim 8 wherein said supernodulation phenotype is conveyed by a recessive mutation.

11. The mutant soybean plant of claim 8 produced by mutation of *Glycine max* cv. Bragg.

12. The mutant soybean plant of claim 8 produced by mutation of *Glycine max* cv. Williams.

13. The mutant soybean plant of claim 8 wherein said mutant soybean plant can be classified into the same genetic complementation group as a mutant variety selected from the group consisting of nts246, nts382, nts2062, nts1116 and nts1007.

14. The mutant soybean plant of claim 8 wherein said mutant soybean plant can be classified into the same genetic complementation group as a mutant variety selected from the group consisting of nts246, nts733, nts382, nts501, nts1007 and nts1116.

15. The mutant soybean of claim 8 that is a mutant variety selected from the group consisting of nts246, nts382, nts1116 and nts65.

16. A mutant soybean plant carrying a mutation that will result in progeny that have nitrate-tolerant nodulation as a distinguishing phenotype wherein the mutation, which conveys the nitrate-tolerant nodulation phenotype of said progeny, is stable from one generation to the next and wherein said phenotype is observable in said progeny as:

(a) an increase in nitrogen-fixing capacity or efficiency of individual nodules compared to wildtype in a support medium having a nitrate level of about 5–6

(b) nodule mass per plant greater than wild-type and a normal nodule number compared to wild-type, when said progeny and wild-type are grown in the presence of 5 mM nitrate; or (c) nodule number and nodule mass in said progeny grown on 5 mM nitrate ranging from equal to or greater than wild-type grown in the absence of nitrate.

17. The mutant soybean plant of claim 16 wherein said progeny can be classified into the same phenotype group as a mutant variety selected from the group consisting of nts382, nts2062, nts2282, nts246, nts65, nts1116, nts2264, nts1007, nts97, nts183, nts225, nts501, nts733, nts739, and nts761.

18. The mutant soybean of claim 16 wherein said progeny can be classified into the same genetic complementation group as a mutant variety selected from the group consisting of nts382, nts246 and nts1116.

19. A mutant soybean plant carrying a mutation that will result in progeny that have supernodulation as a distinguishing phenotype.

20. The mutant soybean plant of claim 19 wherein said progeny can be classified into the same phenotype group as a mutant variety selected from the group consisting of nts382, nts2062, nts2282, nts246, nts65, nts1116, nts2264, nts1007, nts97, nts183, nts225, nts501, nts733, nts739, and nts761.

21. The mutant soybean of claim 19 wherein said progeny can be classified into the same genetic complementation group as a mutant variety selected from the group consisting of nts382, nts246 and nts1116.

22. The mutant soybean plant of claim 1 wherein nodule number and nodule mass of said mutant when grown in a support medium containing 5 mM nitrate range from equal to or greater than wild-type grown in the absence of nitrate.

23. The mutant soybean plant of claim 1 wherein said mutant exhibits an increase in nitrogen-fixing capacity or efficiency of individual nodules compared to the wild-type parent strain when said mutant and said wild-type are grown in the presence of a support medium containing about 5–6 mM nitrate.

24. The mutant soybean plant of claim 1 wherein said mutant exhibits nodule mass per plant greater than wild-type and a normal nodule number compared to wild-type, when said mutant and said wild-type are grown in the presence of 5 mM nitrate.

25. The mutant soybean plant of claim 16 wherein said progeny exhibit an increase in nitrogen-fixing capacity or efficiency of individual nodules compared to said wild-type parent of said mutant in the presence of a support medium containing about 5–6 mM nitrate.

26. The mutant soybean plant of claim 16 wherein said progeny exhibit nodule mass per plant greater than wild-type and a normal nodule number compared to wild-type, when grown in the presence of 5 mM nitrate.

27. The mutant soybean plant of claim 16 wherein said progeny exhibit nodule number and nodule mass, when grown on 5 mM nitrate, ranging from equal to or greater than wild-type grown in the absence of nitrate.

28. The mutant soybean plant of claim 16 produced by mutation of *Glycine max* cv. Bragg.

29. The mutant soybean plant of claim 16 produced by mutation of *Glycine max* cv. Williams.

* * * * *